US012576126B2

(12) United States Patent
Lee et al.

(10) Patent No.: US 12,576,126 B2
(45) Date of Patent: Mar. 17, 2026

(54) NANOEMULSION OPHTHALMIC COMPOSITION COMPRISING CYCLOSPORINE AND MENTHOL, AND PREPARATION METHOD THEREOF

(71) Applicant: TAEJOON PHARMACEUTICAL CO., LTD., Seoul (KR)

(72) Inventors: Joon Youb Lee, Seoul (KR); Youn Jae Shin, Suwon-si (KR); Hyun Won Seo, Jeonju-si (KR); Dae Hun Kim, Suwon-si (KR)

(73) Assignee: TAEJOON PHARMACEUTICAL CO., LTD., Seoul (KR)

( * ) Notice: Subject to any disclaimer, the term of this patent is extended or adjusted under 35 U.S.C. 154(b) by 962 days.

(21) Appl. No.: 17/641,793

(22) PCT Filed: Sep. 4, 2020

(86) PCT No.: PCT/KR2020/011977
§ 371 (c)(1),
(2) Date: Mar. 9, 2022

(87) PCT Pub. No.: WO2021/049825
PCT Pub. Date: Mar. 18, 2021

(65) Prior Publication Data
US 2024/0041974 A1     Feb. 8, 2024

(30) Foreign Application Priority Data

Sep. 9, 2019    (KR) ........................ 10-2019-0111776

(51) Int. Cl.
| | |
|---|---|
| *A61K 9/107* | (2006.01) |
| *A61K 9/00* | (2006.01) |
| *A61K 38/13* | (2006.01) |
| *A61K 47/10* | (2017.01) |
| *A61K 47/38* | (2006.01) |
| *A61K 47/44* | (2017.01) |
| *A61P 27/02* | (2006.01) |

(52) U.S. Cl.
CPC ............ *A61K 38/13* (2013.01); *A61K 9/0048* (2013.01); *A61K 47/10* (2013.01); *A61K 47/38* (2013.01); *A61K 47/44* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 5,589,455 A | 12/1996 | Woo et al. | |
| 6,635,796 B2 | 10/2003 | Pal et al. | |
| 7,202,209 B2 | 4/2007 | Chang et al. | |
| 2004/0073686 A1 | 4/2004 | Hurta | |
| 2005/0106271 A1 | 5/2005 | Nakayama et al. | |
| 2005/0215520 A1 | 9/2005 | Liu et al. | |
| 2007/0008894 A1 | 1/2007 | Chang et al. | |
| 2012/0074588 A1 | 3/2012 | Hsiao et al. | |
| 2016/0055550 A1 | 2/2016 | Sundaresan | |
| 2016/0101050 A1 | 4/2016 | Lee et al. | |
| 2018/0098937 A1* | 4/2018 | Horn ...................... A61K 47/02 |
| 2019/0224120 A1 | 7/2019 | Horn | |

FOREIGN PATENT DOCUMENTS

| | | | | |
|---|---|---|---|---|
| CN | 101244256 | * | 8/2008 | ............. A61K 38/13 |
| CN | 105307668 A | | 2/2016 | |
| CN | 105726479 A | | 7/2016 | |
| CN | 110090294 A | | 8/2019 | |
| EP | 3078385 | | 10/2016 | |
| EP | 2845602 B1 | | 10/2017 | |
| EP | 3000474 B1 | | 11/2018 | |
| JP | 2005-530866 | | 10/2005 | |
| JP | 2009-501228 | | 1/2009 | |
| JP | 2016-519162 A | | 6/2016 | |
| JP | 2017-531665 | | 10/2017 | |
| JP | 2018-065823 | | 4/2018 | |
| KR | 10-1996-0021056 | | 7/1996 | |
| KR | 10-0336090 | | 4/2002 | |
| KR | 10-2004-0068204 | | 10/2003 | |
| KR | 10-2004-0098023 | | 11/2004 | |
| KR | 10-0669510 | | 8/2005 | |
| KR | 10-2005-0116368 | | 12/2005 | |
| KR | 10-1492447 | | 2/2015 | |
| KR | 10-2017-0032808 | | 11/2015 | |
| KR | 10-2002-0011985 | | 2/2022 | |
| WO | WO 0000179 A1 | | 1/2000 | |
| WO | WO 03082247 A2 | | 10/2003 | |
| WO | WO 2018071619 A1 | | 4/2007 | |
| WO | WO2012015211 A2 | | 2/2012 | |
| WO | WO 2013/008714 A1 | | 1/2013 | |
| WO | WO 2019/111917 A1 | | 6/2019 | |

OTHER PUBLICATIONS

Lin et al., "dry eye disease: review of diagnostic approaches and treatments," Saudi Journal of ophthalmology 28:173-181 (2014) (Year: 2014).*
Menthol ChemSpider accessed Apr. 4, 2025 at URL chemspider.com/Chemical-Structure.1216.html, 6 pp. (2025). (Year: 2025).*
CN 101244256 A1; English machine translation provided—2008 (Year: 2008).*
English translation International Search Report issued in International Application No. PCT/KR2020/011977, dated Dec. 11, 2020.
International Search Report issued in International Application No. PCT/KR2020/011977, dated Sep. 4, 2020.

(Continued)

*Primary Examiner* — Julie Ha
*Assistant Examiner* — Kristina M Hellman
(74) *Attorney, Agent, or Firm* — pH IP Law

(57) ABSTRACT

The present invention relates to a nanoemulsion ophthalmic composition and a preparation method thereof, wherein the nanoemulsion ophthalmic composition is obtained by mixing cyclosporine, castor oil, hydrophilic and hydrophobic emulsifiers, menthol, and an aqueous solvent, and thus exhibits excellent stability as well as ameliorating ocular irritation such as a feeling of grittiness, blurry vision, and the like.

22 Claims, 2 Drawing Sheets

(56)         References Cited

OTHER PUBLICATIONS

KR Office Communication—Notice of Submission of Opinions (Machine Translation), dated Feb. 1, 2021.
KR Office Communication Grant of Patent (Machine Translation), dated Mar. 30, 2021.
Liu, Chen, et al., "Enhanced skin permeation of glabridin using eutectic mixture-based nanoemulsion." Drug delivery and translational research 7.2 (2017): 325-332.
Office Action issued in Chinese Application No. 202080062721.9 mailed Jul. 15, 2023, and English translation thereof.
Extended European Search Report issued in European Patent Application No. 20862827.1, dated Sep. 6, 2023.
Office Action issued in Japanese Patent Application No. 2022-515794, dated Sep. 3, 2024.

* cited by examiner

NANOEMULSION OPHTHALMIC COMPOSITION COMPRISING CYCLOSPORINE AND MENTHOL, AND PREPARATION METHOD THEREOF

This application is a national phase application under 35 U.S.C. § 371 of International Application No. PCT/KR2020/011977, filed Sep. 4, 2020, which claims priority to Korean Application No. 10-2019-0111776, filed Sep. 9, 2019. The entire text of each of the above referenced disclosures is specifically incorporated herein by reference.

TECHNICAL FIELD

The present invention relates to a nanoemulsion ophthalmic composition comprising cyclosporine, castor oil, hydrophilic emulsifier, hydrophobic emulsifier and menthol, and a method for preparing the same.

BACKGROUND

Cyclosporine is a poorly soluble drug that is hardly dissolved in water, and thus it is very difficult to prepare a water-soluble pharmaceutical composition containing cyclosporine. To date, many efforts have been made to prepare pharmaceutical compositions containing cyclosporine using aqueous and non-aqueous media. For example, Restasis® is commercially available as an eye drop for treating dry eye syndrome containing cyclosporine as an active ingredient, but Restasis® is a colored, opaque emulsion type product, which may cause blurred vision, foreign body sensation, burning sensation, etc.

A nanoemulsion-type eye drop that has improved the above disadvantages has been developed with Korean Patent No. 1492447. The patent document discloses a nanoemulsion composition which includes cyclosporine, castor oil, polyoxyl 35 castor oil, polyethylene glycol and propylene glycol, in which the content of castor oil is at least eight times that of cyclosporine for the production of a stable nanoemulsion.

The above eye drops are the ones administered twice a day containing cyclosporine at a concentration of 0.05%, and it is necessary to provide a composition containing a high concentration of cyclosporine to reduce the number of administration, thereby increasing compliance with medication. However, cyclosporine is an ingredient that causes eye irritation when administered, and there is a problem in which sense of irritation increases with an increasing content. In addition, in order to prepare a stable nanoemulsion from poorly soluble cyclosporin, the content of an oil ingredient needs to be increased with an increasing content of cyclosporine. However, when including an excess of a non-aqueous solvent such as oil, etc., there is a problem in which an instillation thereof may cause pains including irritation to the eye and blurring of the vision.

Thus, there is a need to develop a novel eye drop capable of maintaining and improving stability and alleviating eye irritation while increasing the content of cyclosporine.

DETAILED DESCRIPTION OF THE INVENTION

Technical Problem

An object of the present invention is to provide a nanoemulsion ophthalmic composition comprising cyclosporine with improved stability, bioavailability and eye irritation, and a method for preparing the same.

Technical Solution

The present invention provide a nanoemulsion ophthalmic composition comprising cyclosporine, castor oil, hydrophilic emulsifier, hydrophobic emulsifier and menthol. The nanoemulsion ophthalmic composition of the present invention exhibits excellent stability (in particular, storage stability) and transparent appearance, and causes less pain including irritation to the eye during instillation and does not cause blurred vision during instillation.

The present invention may provide a stable nanoemulsion ophthalmic composition which comprises: cyclosporine; castor oil; polyoxyethylene castor oil; at least one hydrophobic emulsifier selected from the group consisting of polyethylene glycol and propylene glycol; menthol; and an aqueous solvent.

In the present invention, "cyclosporine" may be an active ingredient of the nanoemulsion ophthalmic composition, and may be preferably cyclosporine A or a derivative thereof.

Cyclosporine may be contained in a therapeutically effective amount to achieve the purpose of ameliorating dry eye. In order to achieve the object of the present invention, cyclosporine in the nanoemulsion ophthalmic composition of the present invention may be included in an amount of 0.01 w/v % or more, specifically 0.03 w/v % or more, more specifically 0.05 w/v % or more, more specifically 0.07 w/v % or more, and even more specifically 0.08 w/v % or more, and may be also included in an amount of 0.5 w/v % or less, specifically 0.2 w/v % or less, and more specifically 0.1 w/v % or less. For example, the content of cyclosporine in the nanoemulsion ophthalmic composition of the present invention may be 0.01 w/v % to 0.5 w/v %, 0.01 w/v % to 0.2 w/v %, 0.01 w/v % to 0.1 w/v %, 0.03 w/v % to 0.5 w/v %, 0.03 w/v % to 0.2 w/v %, 0.03 w/v % to 0.1 w/v %, 0.05 w/v % to 0.5 w/v %, 0.05 w/v % to 0.2 w/v %, 0.05 w/v % to 0.1 w/v %, 0.07 w/v % to 0.5 w/v %, 0.07 w/v % to 0.2 w/v %, 0.07 w/v % to 0.1 w/v %, 0.08 w/v % to 0.5 w/v %, 0.08 w/v % to 0.2 w/v %, or 0.08 w/v % to 0.1 w/v %. In one embodiment of the present invention, the content of cyclosporine may be specifically 0.07 w/v % to 0.2 w/v %, more specifically 0.07 w/v % to 0.1 w/v %, and even more specifically 0.08 w/v % to 0.1 w/v %. In another embodiment of the present invention, the cyclosporine in the nanoemulsion ophthalmic composition of the present invention may be included in an amount of 0.05 w/v %, 0.08 w/v %, or 0.1 w/v %.

The composition of the present invention may comprise castor oil as a non-aqueous solvent. Castor oil used herein may be, for example, the one commercially available under the product name of Castor oil (ITHO oil chem, Japan). Castor oil may reduce the evaporation of tears on the surface of the eyeball and have excellent spreading ability compared to other oils, and thus it may be helpful in the treatment of dry eye such as Meibomian gland dysfunction of the lacrimal gland, etc.

However, castor oil may cause pain including eye irritation, and blurred vision. Thus, the castor oil included in the composition of the present invention may be preferably used at a minimum concentration capable of well dissolving cyclosporine and minimizing ocular adverse reactions. Accordingly, the amount of the emulsifier used to stabilize an oil phase may be minimized, thereby providing a nanoemulsion composition for ophthalmic uses, which is safer than existing cyclosporine emulsions. In one embodiment of the present invention, a content ratio of cyclosporine and castor oil (w:w) in the nanoemulsion ophthalmic composition of the present invention may be 1:2.5 or more, 1:more than 2.5 and 1:3 or more, and may be 1:less than 8, particularly 1:less than 5 and 1:4.7 or less. In one embodiment of the present invention, a content ratio of cyclosporine and castor oil (w:w) in the nanoemulsion ophthalmic composition of the present invention may be 1:3 or more and 1:less than 5, specifically 1:3 or more and 1:4.7 or less. The present inventors have reduced the content of castor oil required to prepare a stable nanoemulsion from poorly soluble cyclosporine to less than eight times, particularly less than five times that of cyclosporine, thereby minimizing the induction of pain including eye irritation, and blurred vision.

Specifically, the content of castor oil in the present invention may be more than 2.5 times or at least three times that of cyclosporine included in the composition. In the present invention, the content of castor oil may be 4.1 times that of cyclosporine included in the composition. In the present invention, the content of castor oil may be 0.2 w/v % or more and more than 0.2 w/v %, specifically 0.25 w/v % or more, and more specifically 0.3 w/v % or more, based on the total content of the composition. In addition, the content of castor oil in the present invention may be less than five times, and may be 4.7 times or less that of cyclosporine included in the composition. Moreover, the content of castor oil in the present invention may be less than 0.4 w/v % or 0.375 w/v % or less based on the total content of the composition. In the present invention, the content of castor oil may be 0.325 w/v %.

In one embodiment of the present invention, the content of castor oil may be three times or more and less than five times, three times or more and 4.7 times or less, for example, 4.1 times that of cyclosporine included in the composition. For example, the content of castor oil in the nanoemulsion ophthalmic composition of the present invention may be more than 0.2 w/v % and less than 0.4 w/v %, more than 0.2 w/v % and 0.375 w/v % or less, 0.25 w/v % or more and less than 0.4 w/v %, 0.25 w/v % or more and 0.375 w/v % or less, 0.3 w/v % or more and less than 0.4 w/v %, 0.3 w/v % or more and 0.375 w/v % or less, and 0.325 w/v %. For example, the content of castor oil in the present invention may be more than 0.2 w/v % and less than five times that of cyclosporine included in the composition, 0.25 w/v % or more and less than five times that of cyclosporine included in the composition, 0.3 w/v % or more and less than five times that of cyclosporine included in the composition, more than 0.2 w/v % and 4.7 times or less that of cyclosporine included in the composition, 0.25 w/v % or more and 4.7 times or less that of cyclosporine included in the composition, 0.3 w/v % or more and 4.7 times or less that of cyclosporine included in the composition, three times or more that of cyclosporine included in the composition and less than 0.4 w/v %, and three times or more that of cyclosporine included in the composition and 0.375 w/v % or less.

The nanoemulsion ophthalmic composition of the present invention may comprise at least one emulsifier that helps emulsify castor oil in an aqueous solvent. At least one emulsifier may be selected to suit the ratio of the HLB values of each emulsifier according to the required HLB value of castor oil. The emulsifier may be at least one selected from hydrophilic emulsifiers having an HLB (Hydrophilic-Lipo-philic Balance) value of at least 8, particularly 10 or more, and may be at least one selected from hydrophobic emulsifiers having an HLB value of less than 8, particularly 6 or less. The emulsifier of the present invention may be a hydrophilic emulsifier, a hydrophobic emulsifier, or a mixture thereof. In one embodiment of the present invention, it is characterized in that a hydrophilic emulsifier and a hydrophobic emulsifier are used in combination to improve an average particle size, a particle distribution and stability of the nanoemulsion composition.

In the present invention, the hydrophilic emulsifier may be polyoxyethylene castor oil, preferably polyoxyl 35 castor oil, which is commercially available under the product name of Cremophor EL™. The content of the hydrophilic emulsifier may be 1 w/v % to 5 w/v % based on the total content of the composition.

In the present invention, the content of the hydrophilic emulsifier may be 1.4 w/v % or more, more than 1.4 w/v %, 1.5 w/v % or more, more than 1.5 w/v %, 1.6 w/v % or more, and 1.8 w/v % or more. In the present invention, the content of the hydrophilic emulsifier may be 5 w/v % or less, 4.5 w/v % or less, and 4 w/v % or less.

For example, the content of the hydrophilic emulsifier may be more than 1.4 w/v % and 5 w/v % or less, more than 1.4 w/v % and 4.5 w/v % or less, more than 1.4 w/v % and 4 w/v % or less, 1.5 w/v % or more and 5 w/v % or less, 1.5 w/v % or more and 4.5 w/v % or less, 1.5 w/v % or more and 4 w/v % or less, more than 1.5 w/v % and 5 w/v % or less, more than 1.5 w/v % and 4.5 w/v % or less, more than 1.5 w/v % and 4 w/v % or less, 1.6 w/v % or more and 5 w/v % or less, 1.6 w/v % or more and 4.5 w/v % or less, 1.6 w/v % or more and 4 w/v % or less, 1.8 w/v % or more and 5 w/v % or less, 1.8 w/v % or more and 4.5 w/v % or less, and 1.8 w/v % or more and 4 w/v % or less.

When the hydrophilic emulsifier is included in the nanoemulsion composition of the present invention in the same amount as above, it may be possible to more easily form a stable nanoemulsion having an average particle size of 1 nm to 100 nm, and the hydrophilic emulsifier may be included in an amount of 5 w/v % or less, thereby providing excellent sensation of instillation.

Meanwhile, the hydrophobic emulsifier of the present invention may be ionic or nonionic, but may be preferably nonionic. The hydrophobic emulsifier used herein may be polyethylene glycol, propylene glycol, or a mixture thereof, which may be commercially available under the product name of Super refined PEG 300™, Super refined PEG 400™, Super refined PEG 600™ (Croda), and propylene glycol (Merck), respectively. The content of the hydrophobic emulsifier may be 0.1 w/v % to 5 w/v %.

Specifically, the content of the hydrophobic emulsifier in the nanoemulsion ophthalmic composition of the present invention may be 0.2 w/v % or more, specifically more than 0.2 w/v %, and more specifically 0.3 w/v % or more, and may be more specifically 0.4 w/v % or more, 0.5 w/v % or more, and even more specifically 0.7 w/v % or more. Moreover, in the present invention, the content of the hydrophobic emulsifier may be 5 w/v % or less, specifically 4.5 w/v % or less, and more specifically 4 w/v % or less.

For example, in the present invention, the content of the hydrophobic emulsifier may be 0.2 w/v % to 5 w/v %, 0.2 w/v % to 4.5 w/v %, 0.2 w/v % to 4 w/v %, more than 0.2 w/v % and 5 w/v % or less, more than 0.2 w/v % and 4.5 w/v % or less, more than 0.2 w/v % and 4 w/v % or less, 0.3 w/v % to 5 w/v %, 0.3 w/v % to 4.5 w/v %, 0.3 w/v % to 4 w/v %, 0.4 w/v % to 5 w/v %, 0.4 w/v % to 4.5 w/v %, 0.4 w/v % to 4 w/v %, 0.5 w/v % to 5 w/v %, 0.5 w/v % to 4.5 w/v %, 0.5 w/v % to 4 w/v %, 0.7 w/v % to 5 w/v %, 0.7 w/v % to 4.5 w/v %, and 0.7 w/v % to 4 w/v %.

5

6

The nanoemulsion ophthalmic composition of the present invention may specifically comprise polyoxyethylene castor oil in an amount of 1 w/v % to 5 w/v % and at least one hydrophobic emulsifier selected from the group consisting of polyethylene glycol and propylene glycol in an amount of 0.1 w/v % to 5 w/v %.

More specifically, the content of polyoxyethylene castor oil in the nanoemulsion ophthalmic composition of the present invention may be more than 1.4 w/v % and 5 w/v % or less, more than 1.4 w/v % and 4.5 w/v % or less, more than 1.4 w/v % and 4 w/v % or less, 1.5 w/v % or more and 5 w/v % or less, 1.5 w/v % or more and 4.5 w/v % or less, 1.5 w/v % or more and 4 w/v % or less, more than 1.5 w/v % and 5 w/v % or less, more than 1.5 w/v % and 4.5 w/v % or less, more than 1.5 w/v % and 4 w/v % or less, 1.6 w/v % or more and 5 w/v % or less, 1.6 w/v % or more and 4.5 w/v % or less, 1.6 w/v % or more and 4 w/v % or less, 1.8 w/v % or more and 5 w/v % or less, 1.8 w/v % or more and 4.5 w/v % or less, and 1.8 w/v % or more and 4 w/v % or less. The content of the hydrophobic emulsifier may be 0.2 w/v % to 5 w/v %, 0.2 w/v % to 4.5 w/v %, 0.2 w/v % to 4 w/v %, more than 0.2 w/v % and 5 w/v % or less, more than 0.2 w/v % and 4.5 w/v % or less, more than 0.2 w/v % and 4 w/v % or less, 0.3 w/v % to 5 w/v %, 0.3 w/v % to 4.5 w/v %, 0.3 w/v % to 4 w/v %, 0.4 w/v % to 5 w/v %, 0.4 w/v % to 4.5 w/v %, 0.4 w/v % to 4 w/v %, 0.5 w/v % to 5 w/v %, 0.5 w/v % to 4.5 w/v %, 0.5 w/v % to 4 w/v %, 0.7 w/v % to 5 w/v %, 0.7 w/v % to 4.5 w/v %, and 0.7 w/v % to 4 w/v %.

The present inventors have found that menthol may be added to the nanoemulsion composition to maintain or improve the stability of the nanoemulsion composition, and to maintain the content of castor oil to less than eight times, for example, less than five times that of cyclosporine while increasing the concentration of cyclosporine in the nanoemulsion ophthalmic composition. In general, an increasing content of castor oil may cause the side effect of increased eye irritation. However, the nanoemulsion ophthalmic composition according to the present invention may dissolve poorly soluble cyclosporine well, show improved storage stability and excellent bioavailability and solve or alleviate side effects such as eye irritation, foreign body sensation, and blurred vision, though the content of castor oil in the composition is limited to less than eight times, for example, less than five times, that of cyclosporine.

Specifically, the present inventors have confirmed that the storage stability of the cyclosporine nanoemulsion composition is improved with the addition of menthol to the nanoemulsion composition in that the degree of decrease in the cyclosporine content is remarkably less and a particle size is stably maintained even under stress conditions. In particular, the present inventors have confirmed that stability is reduced when menthol is not included in the nanoemulsion composition, thereby suggesting that menthol is essential for maintaining stability, and have also confirmed for the first time that the effect of stabilizing the cyclosporine nanoemulsion composition is rather reduced with an excessive content of menthol contained in the nanoemulsion composition, thereby suggesting that an optimal content of menthol is essential for maintaining the stability of the cyclosporine nanoemulsion composition. In addition, it has been confirmed that an excellent sensation of instillation is provided when menthol is included in an amount of less than 0.1 w/v %, for example, in an amount of 0.01 w/v % or less.

In the present invention, the content of menthol may be 0.001 w/v % or more, specifically 0.002 w/v % or more. In the present invention, the content of menthol may be less than 0.1 w/v %, specifically 0.05 w/v % or less, 0.01 w/v % or less, and more specifically 0.005 w/v % or less.

For example, in the present invention, the content of menthol may be 0.001 w/v % or more and less than 0.1 w/v %, 0.001 w/v % to 0.05 w/v %, 0.001 w/v % to 0.01 w/v %, 0.001 w/v % to 0.005 w/v %, 0.002 w/v % or more and less than 0.1 w/v %, 0.002 w/v % to 0.05 w/v %, 0.002 w/v % to 0.01 w/v %, 0.002 w/v % to 0.005 w/v %, and 0.0025 w/v %.

The present invention may provide a stable nanoemulsion ophthalmic composition which is prepared by mixing: cyclosporine; castor oil; polyoxyethylene castor oil; at least one hydrophobic emulsifier selected from the group consisting of polyethylene glycol and propylene glycol; menthol; and an aqueous solvent in an amount thereof described above.

In one embodiment of the present invention, the present invention may provide a nanoemulsion ophthalmic composition which comprises: cyclosporine in an amount of 0.03 w/v % to 0.5 w/v %; castor oil in an amount of 0.2 w/v % or more and less than eight times the content of cyclosporine; polyoxyethylene castor oil in an amount of 1 w/v % to 5 w/v %; at least one hydrophobic emulsifier selected from the group consisting of polyethylene glycol and propylene glycol in an amount of 0.1 w/v % to 5 w/v %; menthol in an amount of 0.001 w/v % or more and less than 0.1 w/v %; and an aqueous solvent.

In another embodiment of the present invention, the present invention may provide a nanoemulsion ophthalmic composition which comprises: cyclosporine in an amount of 0.07 w/v % to 0.2 W/17%; castor oil in an amount of 0.25 w/v % or more and less than five times the content of cyclosporine; polyoxyethylene castor oil in an amount of more than 1.4 w/v % to 5 w/v %; polyethylene glycol and/or propylene glycol in an amount of 0.2 w/v % to 5 w/v %; menthol in an amount of 0.001 w/v % to 0.05 w/v %; and an aqueous solvent.

In still another embodiment of the present invention, the present invention may provide a nanoemulsion ophthalmic composition which comprises: cyclosporine in an amount of 0.07 w/v % to 0.2 w/v %; castor oil in an amount of 0.25 w/v % or more and less than five times the content of cyclosporine; polyoxyethylene castor oil in an amount of 1.5 w/v % to 5 w/v %; polyethylene glycol and/or propylene glycol in an amount of 0.3 w/v % to 5 w/v %; menthol in an amount of 0.001 w/v % or more and less than 0.1 w/v %; and an aqueous solvent.

In still another embodiment of the present invention, the present invention may provide a nanoemulsion ophthalmic composition which comprises: cyclosporine in an amount of 0.08 w/v % to 0.1 w/v %; castor oil in an amount of 0.25 w/v % or more and less than five times the content of cyclosporine; polyoxyethylene castor oil in an amount of 1.5 w/v % to 5 w/v %; polyethylene glycol and/or propylene glycol in an amount of 0.3 w/v % to 5 w/v %; menthol in an amount of 0.001 w/v % to 0.01 w/v %; and an aqueous solvent.

In another embodiment of the present invention, the present invention may provide a nanoemulsion ophthalmic composition which comprises: cyclosporine in an amount of 0.08 w/v % to 0.1 w/v %; castor oil in an amount of 0.25 w/v % or more and 4.7 times or less the content of cyclosporine; polyoxyethylene castor oil in an amount of 1.6 w/v % to 5 w/v %; polyethylene glycol and/or propylene glycol in an amount of 0.5 w/v % to 5 w/v %; menthol in an amount of 0.001 w/v % to 0.005 w/v %; and an aqueous solvent.

In still another embodiment of the present invention, the present invention may provide a nanoemulsion ophthalmic composition which comprises: cyclosporine in an amount of 0.08 w/v % to 0.1 w/v %; castor oil in an amount of 0.25 w/v % or more and 4.7 times or less the content of cyclosporine; polyoxyethylene castor oil in an amount of 1.6 w/v % to 5 w/v %; polyethylene glycol and/or propylene glycol in an amount of 0.7 w/v % to 5 w/v %; menthol in an amount of 0.001 w/v % to 0.005 w/v %; and an aqueous solvent.

In one embodiment of the present invention, the present invention may provide a nanoemulsion ophthalmic composition which is prepared by mixing: cyclosporine; castor oil; polyoxyethylene castor oil; at least one hydrophobic emulsifier selected from the group consisting of polyethylene glycol and propylene glycol; menthol; and an aqueous solvent.

In another embodiment of the present invention, the present invention may provide a nanoemulsion ophthalmic composition which is prepared by mixing: cyclosporine in an amount of 0.03 w/v % to 0.5 w/v %; castor oil in an amount of 0.2 w/v % or more and less than eight times the content of cyclosporine; polyoxyethylene castor oil in an amount of 1 w/v % to 5 w/v %; at least one hydrophobic emulsifier selected from the group consisting of polyethylene glycol and propylene glycol in an amount of 0.1 w/v % to 5 w/v %; menthol in an amount of 0.001 w/v % or more and less than 0.1 w/v %; and an aqueous solvent.

In another embodiment of the present invention, the present invention may provide a nanoemulsion ophthalmic composition which is prepared by mixing: cyclosporine in an amount of 0.07 w/v % to 0.2 w/v %; castor oil in an amount of 0.25 w/v % or more and less than five times the content of cyclosporine; polyoxyethylene castor oil in an amount of more than 1.4 w/v % to 5 w/v %; polyethylene glycol and/or propylene glycol in an amount of 0.2 w/v % to 5 w/v %; menthol in an amount of 0.001 w/v % to 0.05 w/v %; and an aqueous solvent.

In another embodiment of the present invention, the present invention may provide a nanoemulsion ophthalmic composition which is prepared by mixing: cyclosporine in an amount of 0.07 w/v % to 0.2 w/v %; castor oil in an amount of 0.25 w/v % or more and less than five times the content of cyclosporine; polyoxyethylene castor oil in an amount of 1.5 w/v % to 5 w/v %; polyethylene glycol and/or propylene glycol in an amount of 0.3 w/v % to 5 w/v %; menthol in an amount of 0.001 w/v % or more and less than 0.1 w/v %; and an aqueous solvent.

In still another embodiment of the present invention, the present invention may provide a nanoemulsion ophthalmic composition which is prepared by mixing: cyclosporine in an amount of 0.08 w/v % to 0.1 w/v %; castor oil in an amount of 0.25 w/v % or more and less than five times the content of cyclosporine; polyoxyethylene castor oil in an amount of 1.5 w/v % to 5 w/v %; polyethylene glycol and/or propylene glycol in an amount of 0.3 w/v % to 5 w/v %; menthol in an amount of 0.001 w/v % to 0.01 w/v %; and an aqueous solvent.

In another embodiment of the present invention, the present invention may provide a nanoemulsion ophthalmic composition which is prepared by mixing: cyclosporine in an amount of 0.08 w/v % to 0.1 w/v %; castor oil in an amount of 0.25 w/v % or more and 4.7 times or less the content of cyclosporine; polyoxyethylene castor oil in an amount of 1.6 w/v % to 5 w/v %; polyethylene glycol and/or propylene glycol in an amount of 0.5 w/v % to 5 w/v %; menthol in an amount of 0.001 w/v % to 0.005 w/v %; and an aqueous solvent.

In still another embodiment of the present invention, the present invention may provide a nanoemulsion ophthalmic composition which is prepared by mixing: cyclosporine in an amount of 0.08 w/v % to 0.1 w/v %; castor oil in an amount of 0.25 w/v % or more and 4.7 times or less the content of cyclosporine; polyoxyethylene castor oil in an amount of 1.6 w/v % to 5 w/v %; polyethylene glycol and/or propylene glycol in an amount of 0.7 w/v % to 5 w/v %; menthol in an amount of 0.001 w/v % to 0.005 w/v %; and an aqueous solvent.

In addition, the nanoemulsion ophthalmic composition of the present invention may further comprise a stabilizer. In case of further including the stabilizer, the nanoemulsion ophthalmic composition of the present invention may have much improvement in the physical and chemical stability thereof. The stabilizer may be hydrated in an aqueous solvent to form a certain bonding structure, thereby having the effect of rasterizing the oil droplets of the nanoemulsion, and thus may play a role in physically stabilizing the nanoemulsion. The stabilizer may include: cellulose-based compounds including carboxymethyl cellulose (CMC), hydroxypropyl methylcellulose (HPMC), hydroxyethyl cellulose (HEC), etc.; polyvinyl-based compounds including polyvinyl alcohol (PVA), polyvinyl pyrrolidone (PVP), etc.; acrylic-based compounds including carbomer, etc.; gums-based compounds including gellan gum, xanthan gum, etc.; polysaccharides including hyaluronic acid (HA), sodium hyaluronate, sodium alginate, dextran, etc.; any combination thereof; or the like. In addition, the stabilizer may be at least one selected from the group consisting of carboxymethyl cellulose (CMC), xanthan gum, hyaluronic acid (HA) and sodium hyaluronate. The content of the stabilizer may be in the range of 0.001 to 10 w/v %, 0.01 to 5 w/v %, preferably 0.01 to 2 w/v %.

In addition, the nanoemulsion ophthalmic composition of the present invention may further comprise a pH adjuster, an isotonic agent, preservatives, a buffer agent, etc. The pH adjuster used herein may be sodium hydroxide, hydrochloric acid, etc., and may be added in an amount required to obtain an appropriate pH according to a method known to those skilled in the art. The isotonic agent used herein may be at least one of glycerol, mannitol, sorbitol, sodium chloride, potassium chloride, boric acid and borax, and a content thereof may be in the range of 0.01 w/v % to 10 w/v %, and may be used in an amount of 0.1 w/v % to 3 w/v %.

The preservatives of the present invention may include: quaternary ammonium compounds including benzalkonium chloride, benzethonium chloride, cetalkonium chloride, polyquaternium-1 (e.g., Polyquad), etc.; guanidine-based compounds including PHMB, chlorohexidine, etc.; chlorobutanol; mercury-based preservatives including thiomersal, phenylmercuric acetate, phenylmercuric nitrate and the like; and oxidative preservatives including a stabilized oxychloro complex (e.g., Purite), p-hydroxybenzoate alkyls (e.g., methyl p-hydroxybenzoate (PM), etc.

The buffer agent of the present invention used herein may be any buffer agent used in eye drops, such as, but not limited thereto, an acetic acid and/or salts thereof, a citric acid and/or salts thereof, a phosphoric acid and/or salts thereof (e.g., sodium hydrogen phosphate and/or hydrates thereof, sodium dihydrogen phosphate and/or hydrates thereof), a boric acid and/or salts thereof. An amount of the buffer agent used herein may be appropriately selected by those skilled in the art, and may be added in an amount of 0.001 to 10 w/v %, specifically 0.01 to 5 w/v %, and more specifically 0.1 to 2 w/v %.

The aqueous solvent of the present invention may refer to an ingredient suitable for the preparation of an ophthalmic formulation, and may be, for example, sterile purified water, physiological saline, or water for injection.

The composition of the present invention may be a nanoemulsion ophthalmic composition having an average particle size of 1 nm or more to 100 nm or less. The particle size of the nanoemulsion ophthalmic composition may be measured using a particle size measuring device, a Zetasizer (e.g., Malvern Zetasizer, Zetasizer Nano $ZS_{90}$, etc.).

The nanoemulsion ophthalmic composition of the present invention may be a composition in which a high concentration of cyclosporine is included to reduce the number of administration, for example, a composition administered once a day.

The present invention may provide a method for preparing a nanoemulsion ophthalmic composition which comprises preparing a mixed composition by stirring and mixing: cyclosporine; castor oil; a hydrophilic emulsifier including polyoxyethylene castor oil; at least one hydrophobic emulsifier selected from the group consisting of polyethylene glycol and propylene glycol; menthol; and an aqueous solvent.

The present invention may also provide a method for preparing a nanoemulsion ophthalmic composition which comprises preparing a mixed composition by stirring and mixing: cyclosporine in an amount of 0.03 w/v % to 0.5 w/v %; castor oil in an amount of 0.2 w/v % or more and less than eight times the content of cyclosporine; a hydrophilic emulsifier including polyoxyethylene castor oil in an amount of 1 w/v % to 5 w/v %; at least one hydrophobic emulsifier selected from the group consisting of polyethylene glycol and propylene glycol in an amount of 0.1 w/v % to 5 w/v %; menthol in an amount of 0.001 w/v % or more and less than 0.1 w/v %; and an aqueous solvent.

The present invention may also provide a method for preparing a nanoemulsion ophthalmic composition which comprises preparing a mixed composition by stirring and mixing: cyclosporine in an amount of 0.07 w/v % to 0.2 w/v %; castor oil in an amount of 0.25 w/v % or more and less than five times the content of cyclosporine; polyoxyethylene castor oil in an amount of more than 1.4 w/v % to 5 w/v %; polyethylene glycol and/or propylene glycol in an amount of 0.2 w/v % to 5 w/v %; menthol in an amount of 0.001 w/v % to 0.05 w/v %; and an aqueous solvent.

The present invention may also provide a method for preparing a nanoemulsion ophthalmic composition which comprises preparing a mixed composition by stirring and mixing: cyclosporine in an amount of 0.07 w/v % to 0.2 w/v %; castor oil in an amount of 0.25 w/v % or more and less than five times the content of cyclosporine; polyoxyethylene castor oil in an amount of 1.5 w/v % to 5 w/v %; polyethylene glycol and/or propylene glycol in an amount of 0.3 w/v % to 5 w/v %; menthol in an amount of 0.001 w/v % or more and less than 0.1 w/v %; and an aqueous solvent.

The present invention may also provide a method for preparing a nanoemulsion ophthalmic composition which comprises preparing a mixed composition by stirring and mixing: cyclosporine in an amount of 0.08 w/v % to 0.1 w/v %; castor oil in an amount of 0.25 w/v % or more and 4.7 times or less the content of cyclosporine; polyoxyethylene castor oil in an amount of 1.6 w/v % to 5 w/v %; polyethylene glycol and/or propylene glycol in an amount of 0.7 w/v % to 5 w/v %; menthol in an amount of 0.001 w/v % to 0.005 w/v %; and an aqueous solvent.

The present invention may also provide a method for preparing a nanoemulsion ophthalmic composition which comprises preparing a mixed composition by stirring and mixing: cyclosporine in an amount of 0.03 w/v % to 0.5 w/v %; castor oil in an amount of 0.2 w/v % or more and less than eight times the content of cyclosporine; a hydrophilic emulsifier including polyoxyethylene castor oil in an amount of 1 w/v % to 5 w/v %; at least one hydrophobic emulsifier selected from the group consisting of polyethylene glycol and propylene glycol in an amount of 0.1 w/v % to 5 w/v %; menthol in an amount of 0.001 w/v % or more and less than 0.1 w/v %; and an aqueous solvent.

The present invention may also provide a method for preparing a nanoemulsion ophthalmic composition which comprises preparing a mixed composition by stirring and mixing: cyclosporine in an amount of 0.07 w/v % to 0.2 w/v %; castor oil in an amount of 0.25 w/v % or more and less than five times the content of cyclosporine; polyoxyethylene castor oil in an amount of more than 1.4 w/v % to 5 w/v %; polyethylene glycol and/or propylene glycol in an amount of 0.2 w/v % to 5 w/v %; menthol in an amount of 0.001 w/v % to 0.05 w/v %; and an aqueous solvent.

The present invention may also provide a method for preparing a nanoemulsion ophthalmic composition which comprises preparing a mixed composition by stirring and mixing: cyclosporine in an amount of 0.08 w/v % to 0.1 w/v %; castor oil in an amount of 0.25 w/v % or more and 4.7 times or less the content of cyclosporine; polyoxyethylene castor oil in an amount of 1.6 w/v % to 5 w/v %; polyethylene glycol and/or propylene glycol in an amount of 0.7 w/v % to 5 w/v %; menthol in an amount of 0.001 w/v % to 0.005 w/v %; and an aqueous solvent.

A nanoemulsion ophthalmic composition having an average particle size of 1 nm to 100 nm may be prepared according to a method for preparing a nanoemulsion ophthalmic composition of the present invention.

In the preparation of the composition, further dissolving an additive such as a stabilizer, an isotonic agent or the like in an aqueous solvent, mixing with the prepared mixed composition, sufficiently stirring, and adjusting the pH may be further included.

In the method for preparing the nanoemulsion ophthalmic composition, cyclosporine, castor oil, polyoxyethylene castor oil, hydrophilic emulsifier, hydrophobic emulsifier, menthol, aqueous solvent, additives such as stabilizer, isotonic agent, or the like may be the same as described above in the nanoemulsion ophthalmic composition of the present invention, if not contradictory to each other.

In the preparation of the composition, the pH adjustment may be performed with the same pH adjuster and a content thereof as used in the nanoemulsion ophthalmic composition of the present invention.

According to the preparation method of the present invention, a nanoemulsion having an average particle size of 1 nm to 100 nm may be formed by properly mixing the ingredients, and a nanoemulsion ophthalmic composition having a particle size of 220 nm or less may be prepared. Thus, high-speed stirring or high-speed shearing devices such as a conventional high-pressure homogenizer or a microfluidizer may not be used, a conventional sterile filtration method using a 0.22 μm filter may be used, and a nanoemulsion ophthalmic composition having a particle size of 220 nm or less may be prepared at low preparation cost.

The nanoemulsion ophthalmic composition according to the present invention may be prepared, by appropriately mixing the above ingredients, with an average particle size of 200 nm or less, specifically 1 nm or more and 100 nm or less, along with a narrow distribution of particle sizes (particle size distribution), thereby providing advantages of possible filtration through the sterile filtration method as well as better stability.

In the present specification, the description of the nanoemulsion ophthalmic composition may be equally applied to the method for preparing the nanoemulsion ophthalmic composition, if not contradictory to each other.

In another embodiment of the present invention, there may be provided a method for preventing or treating dry eye syndrome, the method comprising administering to a subject a nanoemulsion ophthalmic composition which comprises: cyclosporine in an amount of 0.03 w/v % to 0.5 w/v %; castor oil in an amount of 0.2 w/v % or more and less than eight times the content of cyclosporine; a hydrophilic emulsifier including polyoxyethylene castor oil in an amount of 1 w/v % to 5 w/v %; at least one hydrophobic emulsifier selected from the group consisting of polyethylene glycol and propylene glycol in an amount of 0.1 w/v % to 5 w/v %; menthol in an amount of 0.001 w/v % or more and less than 0.1 w/v %; and an aqueous solvent.

In one embodiment of the present invention, there may be provided a use of a nanoemulsion ophthalmic composition which comprises: cyclosporine in an amount of 0.03 w/v % to 0.5 w/v %; castor oil in an amount of 0.2 w/v % or more and less than eight times the content of cyclosporine; a hydrophilic emulsifier including polyoxyethylene castor oil which includes a high concentration of cyclosporine to reduce the number of administration, for example, once a day.

MODE FOR INVENTION

Figure 1:
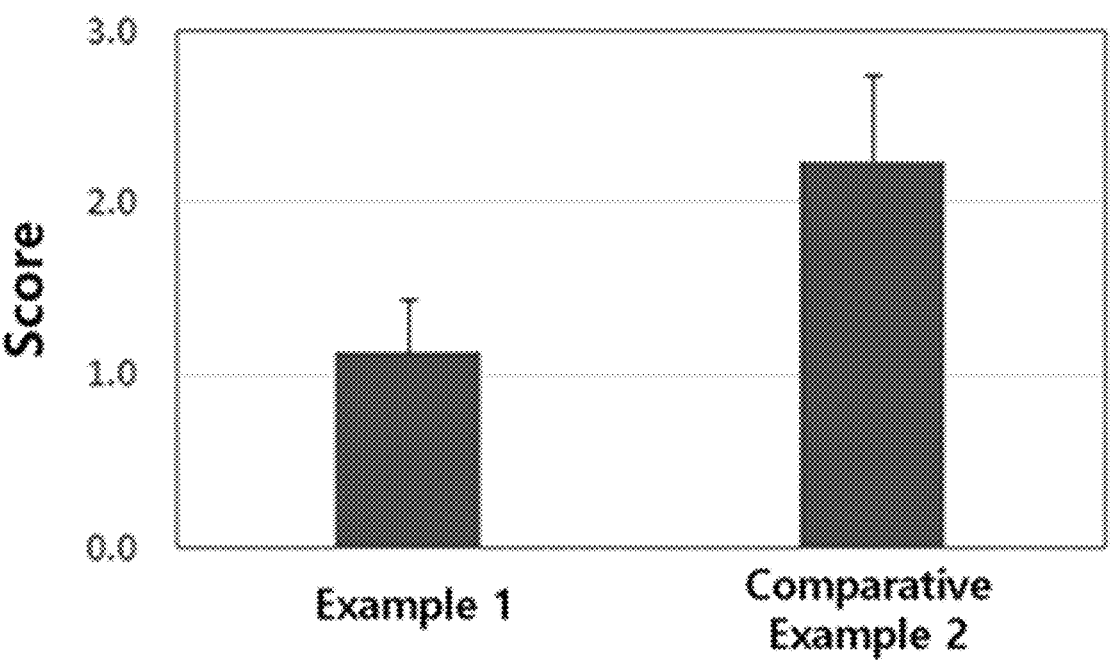
FIG. 1 is a graph showing the results of evaluating an eye irritation of an ophthalmic composition.

Hereinafter, the present invention will be described in detail through preferred Examples for better understanding of the present invention. However, the following Examples are provided only for the purpose of illustrating the present invention, and thus the present invention is not limited thereto.

Experimental Example 1: Confirmation of Storage Stability of Nanoemulsion Composition Ophthalmic compositions were prepared in accordance with ingredients and contents as shown in table 1 below.

TABLE 1

| Ingredient & Content (mg/ml) | Comparative Example 1 | Example 1 | Example 2 | Example 3 | Example 4 |
|---|---|---|---|---|---|
| Cyclosporine A | 0.8 | 0.8 | 0.8 | 0.8 | 0.8 |
| Castor oil | 3.25 | 3.25 | 3.25 | 3.25 | 3.25 |
| Polyoxyl35 castor oil | 18 | 18 | 18 | 18 | 18 |
| Polyethylene glycol 400 | 4 | 4 | 4 | 4 | 4 |
| Propylene glycol | 3 | 3 | 3 | 3 | 3 |
| Sodium carboxymethyl cellulose | 1 | 1 | 1 | 1 | 1 |
| Xanthan gum | 1.5 | 1.5 | 1.5 | 1.5 | 1.5 |
| Glycerin | Appropriate amount | Appropriate amount | Appropriate amount | Appropriate amount | Appropriate amount |
| Boric acid | Appropriate amount | Appropriate amount | Appropriate amount | Appropriate amount | Appropriate amount |
| L-Menthol | 0 | 0.01 | 0.025 | 0.05 | 0.1 | in an amount of 1 w/v % to 5 w/v %; at least one hydrophobic emulsifier selected from the group consisting of polyethylene glycol and propylene glycol in an amount of 0.1 w/v % to 5 w/v %; menthol in an amount of 0.001 w/v % or more and less than 0.1 w/v %; and an aqueous solvent for preparing a medication for preventing or treating dry eye syndrome.

Advantageous Effects

The nanoemulsion composition of the present invention has improved stability (in particular, storage stability) and transparent appearance, and has excellent bioavailability such as ocular retention time, residue, tissue permeability and the like with regard to cyclosporine upon instillation, and alleviated side effects such as eye irritation, foreign body sensation, blurred vision and the like, and thus can be effectively used as a therapeutic agent for dry eye syndrome. In addition, the nanoemulsion composition of the present invention can be effectively used as a therapeutic agent Specifically, castor oil, a hydrophilic emulsifier (polyoxyl 35 castor oil) and a hydrophobic emulsifier (polyethylene glycol 400 and propylene glycol) were mixed and stirred in the amounts as shown in table 1, after which cyclosporin A was added and completely dissolved at 70° C. by using a stirrer. This solution was cooled to a temperature of about 60° C., and then menthol was mixed and dissolved to prepare an oil phase. At the same time, sodium carboxymethyl cellulose and xanthan gum were completely hydrated in water for injection at 70° C. by using a stirrer. The aqueous solution was cooled to room temperature, and dissolved with the addition of an isotonic agent and a buffer, after which pH was adjusted using sodium hydroxide solution and sterilized using an autoclave to prepare an aqueous solution. The oil phase filtered by 0.2 μm was added to the aqueous solution and mixed homogeneously. Water for injection was added to this mixed solution to make a final volume of 100 mL and stirred. Comparative Example 1 was prepared in the same manner as above except for the process of adding menthol. The nanoemulsion was subjected to a self-nanoemulsifying drug delivery system (SNEDDS) to spontaneously form a stable single phase. After that, the prepared compositions were stored under stress conditions (70° C., 55% RH) for four weeks, and then the content of cyclosporine was analyzed.

As a result, it was confirmed that Examples 1 to 4 of the nanoemulsion composition of the present invention containing menthol show a remarkably less degree of decrease in the content after four weeks of storage compared to the initial content of cyclosporine immediately after preparation compared to the composition of Comparative Example 1 (Table 2). The above results show that the nanoemulsion ophthalmic composition of the present invention containing menthol has excellent storage stability and remarkably improved stability compared to the comparative composition not containing menthol.

TABLE 2

| Unit (%) | Comparative Example 1 | Example 1 | Example 2 | Example 3 | Example 4 |
|---|---|---|---|---|---|
| The initial content of immediately after preparation | 99.4 | 99.4 | 99.0 | 99.8 | 99.7 |
| Week 4 | 88.5 | 97.2 | 96.6 | 93.2 | 92.1 |
| Decrease in content | −10.9 | −2.2 | −2.4 | −6.6 | −7.6 |

Experimental Example 2: Evaluation of Eye Irritation

According to the method of Experimental Example 1, ophthalmic compositions were prepared in accordance with ingredients and contents as shown in table 3 below, and sensation of instillation was evaluated. The ophthalmic composition of table 3 was administered into both eyes of eight adults, after which the burning sensation felt in about 30 minutes after administration was scored and evaluated according to the criteria in table 4, and the results are shown in FIG. 1.

14

TABLE 3

| Ingredient & Content (mg/ml) | Example 2 | Comparative Example 2 |
|---|---|---|
| Cyclosporine A | 0.8 | 0.8 |
| Castor oil | 3.25 | 6.4 |
| Polyoxyl35 castor oil | 18 | 18 |
| Polyethylene glycol 400 | 4 | 4 |
| Propylene glycol | 3 | 3 |
| Sodium carboxymethyl cellulose | 1 | 1 |
| Xanthan gum | 1.5 | 1.5 |
| Glycerin | Appropriate amount | Appropriate amount |
| Boric acid | Appropriate amount | Appropriate amount |
| L-Menthol | 0.025 | 0.025 |

TABLE 4

| Burning sensation | Score |
|---|---|
| No unpleasant feeling, very soft | 0 |
| Slightly tingling sensation | 1~2 |
| Slight tingling sensation with mild pain | 3~4 |
| Burning sensation with continuous pain and impossible everyday life | 5 |

As a result, it was found that Comparative Example 2 having a high content of castor oil shows a higher burning sensation than that of Example 1, which is statistically very significant (see FIG. 1).

Experimental Example 3: Confirmation of Storage Stability of Nanoemulsion Composition According to the method of Experimental Example 1, ophthalmic compositions were prepared in accordance with ingredients and contents as shown in table 5 below.

TABLE 5

| Ingredient & Content (w/v %) | Example 5 | Example 6 | Example 7 | Example 8 | Example 9 |
|---|---|---|---|---|---|
| Cyclosporine A | 0.08 | 0.08 | 0.08 | 0.08 | 0.08 |
| Castor oil | 0.325 | 0.325 | 0.25 | 0.275 | 0.375 |
| Polyoxyl35 castor oil | 1.6 | 5 | 1.8 | 1.8 | 1.8 |
| Polyethylene glycol 400 | 0.4 | 0.4 | 0.4 | 0.4 | 0.4 |
| Propylene glycol | 0.3 | 0.3 | 0.3 | 0.3 | 0.3 |
| Sodium carboxymethyl cellulose | 0.1 | 0.1 | 0.1 | 0.1 | 0.1 |
| Xanthan gum | 0.15 | 0.15 | 0.15 | 0.15 | 0.15 |
| Glycerin | Appropriate amount | Appropriate amount | Appropriate amount | Appropriate amount | Appropriate amount |
| Boric acid | Appropriate amount | Appropriate amount | Appropriate amount | Appropriate amount | Appropriate amount |
| L-Menthol | 0.0025 | 0.0025 | 0.0025 | 0.0025 | 0.0025 |

US 12,576,126 B2

15

16

The prepared compositions were stored under a high temperature condition (70° C., 55% RH) for two weeks, and then the content of cyclosporine was measured. In addition, the prepared compositions were stored under a high temperature condition (70° C., 55% RH) for four weeks, and then the particle size of nanoemulsion was analyzed. The particle size of the nanoemulsion was analyzed with a particle size measuring device, Zetasizer (Malvern Instruments, England), after dispersing 200 μL of the nanoemulsion in 2 ml of water for injection.

As a result, it could be confirmed that the particle size and cyclosporine content of the prepared compositions are stably maintained (Table 6). In particular, it was confirmed that the cyclosporine content in all Examples is within the range of 90% to 110% compared to the initial content after storage for two weeks, and the particle size is also maintained at 100 nm or less. Accordingly, it was confirmed that the composition according to one embodiment of the present invention has excellent storage stability.

TABLE 6

|  |  | Exam-ple 5 | Exam-ple 6 | Exam-ple 7 | Exam-ple 8 | Exam-ple 9 |
|---|---|---|---|---|---|---|
| Content (%) | Upon preparation | 100.0 | 100.0 | 100.0 | 100.0 | 100.0 |
|  | Week 2 | 95.4 | 93.0 | 92.0 | 92.0 | 90.0 |
| Particle Size (nm) | Upon preparation | 21.9 | 17.2 | 20.0 | 20.1 | 22.2 |
|  | Week 4 | 25.9 | 20.6 | 22.2 | 22.8 | 76.5 |

Experimental Example 4: Confirmation of Storage Stability of Nanoemulsion Composition According to the method of Experimental Example 1, ophthalmic compositions were prepared in accordance with ingredients and contents as shown in table 7 below.

TABLE 7

| Ingredient & Content (mg/ml) | Example 10 | Example 11 | Example 12 |
|---|---|---|---|
| Cyclosporine A | 0.8 | 0.8 | 0.8 |
| Castor oil | 3.25 | 3.25 | 3.25 |
| Polyoxyl35 castor oil | 18 | 18 | 18 |
| Polyethylene glycol 400 | 5 | 10 | 20 |
| Propylene glycol | 5 | 10 | 20 |
| Sodium carboxymethyl cellulose | 1 | 1 | 1 |
| Xanthan gum | 1.5 | 1.5 | 1.5 |
| Glycerin | Appropriate amount | Appropriate amount | Appropriate amount |
| Boric acid | Appropriate amount | Appropriate amount | Appropriate amount |
| L-Menthol | 0.025 | 0.025 | 0.025 |

The prepared compositions were stored under a stress condition (70° C., 55% RH) for four weeks, and then the content of cyclosporine was analyzed.

As a result, it could be confirmed that the cyclosporine content of the prepared compositions is stably maintained (Table 8).

TABLE 8

| Unit (%) | Example 10 | Example 11 | Example 12 |
|---|---|---|---|
| The initial content of immediately after preparation | 100.7 | 98.7 | 100.8 |
| Week 4 | 91.8 | 92.6 | 92.3 |
| Decrease in content | −8.9 | −6.1 | −8.5 |

Experimental Example 5: Confirmation of Bioavailability of Nanoemulsion Composition Restasis® eye drops commercially available and the ophthalmic composition of Example 2 were instilled once in New Zealand White Rabbit, and pharmacokinetic tests were performed on the cornea and aqueous humor for one day. Currently, Restasis® eye drops are required to be used twice a day. AUC and Cmax of Restasis® eye drops expected in the case of using twice a day, were compared with the results of the ophthalmic composition of Example 2. In the cornea and aqueous humor, it was shown that the AUC of the ophthalmic composition of Example 2 is 1.29 times and 1.56 times higher, respectively, and the Cmax was 3.15 times and 2.96 times higher, respectively compared to the expected AUC and Cmax values of Restasis® eye drops. From the results, it was confirmed that the composition of Example 2 of the present invention has an excellent effect on bioavailability in corneal and aqueous humor compared to Restasis® eye drops even when administered once a day.

TABLE 9

|  | Example 2 | | Restasis ® | |
|---|---|---|---|---|
|  | Cornea | Aqueous humor | Cornea | Aqueous humor |
| AUC (Single injection) | 249.08 | 26.49 | 96.88 | 8.50 |
| $C_{max}$ (Single injection) | 18.25 | 12.04 | 5.79 | 4.07 |
| Described usage | Once/day | | Twice/day | |
| AUC expected value (based on usage) | 249.08 | 26.49 | 193.76 | 17.00 |

Experimental Example 6: Confirmation of Efficacy of Nanoemulsion Composition

Figure 2:
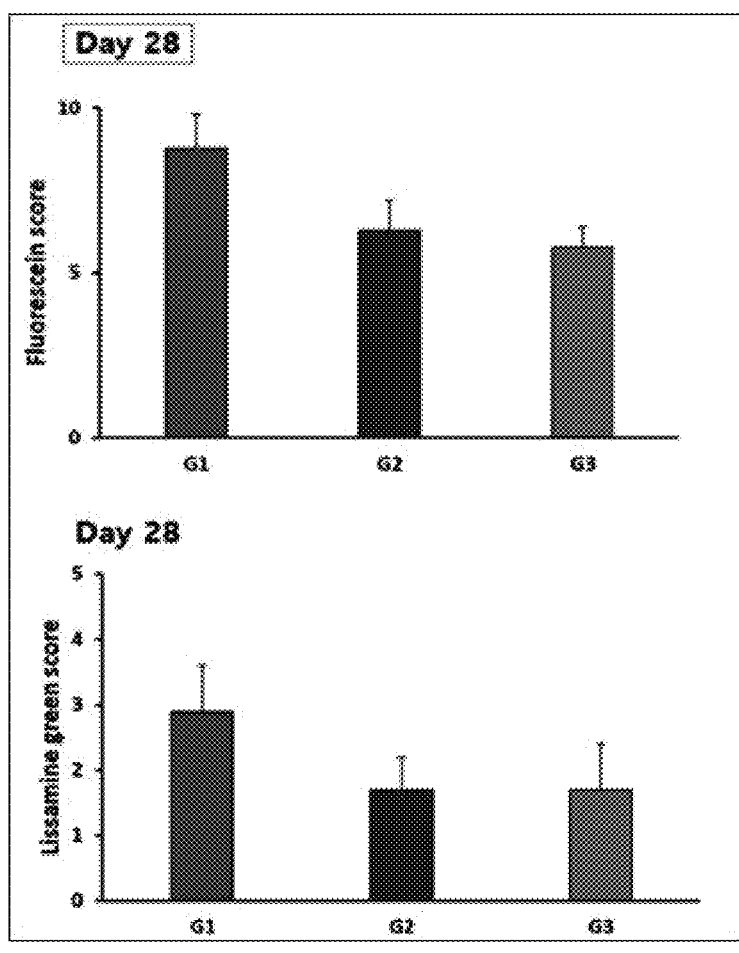
FIG. 2 is a graph showing the results of evaluating an efficacy of an ophthalmic composition.

After inducing dry eye syndrome in New Zealand White Rabbit, the composition of Example 2 and Restasis® eye drops were administered. The treatment effect was confirmed by staining the cornea and conjunctiva of the untreated group (G1), the group dosed once with the composition of Example 2 (G2), and the group dosed twice with Restasis® eye drops (G3). To evaluate the treatment effect, the cornea was stained with fluorescein and the conjunctiva was stained with lissamine green to evaluate staining scores. As a result, it was found that the group G2 shows a significantly lower level of staining scores compared to the group G1 and shows a similar level of staining scores to the group G3 dosed twice with Restasis® eye drops (FIG. 2). The composition of Example 2 requires the less number of administrations and has a lower content of cyclosporine administered according to usage compared to Restasis® eye drops, but provides an equal level of treatment effect on dry eye syndrome. Accordingly, it was confirmed that the composition according to Example 2 shows an improved effect compared to Restasis® eye drops.

The invention claimed is:

1. A stable nanoemulsion ophthalmic composition with low ocular irritation, comprising:
   cyclosporine in an amount of 0.07 w/v % to 0.2 w/v %;
   castor oil in an amount of 0.2 w/v % to less than five times the amount of cyclosporine;
   a hydrophilic emulsifier comprising polyoxyethylene castor oil in an amount of 1 w/v % to 5 w/v %;
   at least one hydrophobic emulsifier selected from the group consisting of polyethylene glycol and propylene glycol in an amount of 0.1 w/v % to 5 w/v %;
   menthol in an amount of 0.001 w/v % to less than 0.1 w/v %; and
   an aqueous solvent.

2. The nanoemulsion ophthalmic composition of claim 1, wherein the castor oil is in an amount of 0.25 w/v % to less than five times the amount of cyclosporine.

3. The nanoemulsion ophthalmic composition of claim 1, wherein the polyoxyethylene castor oil is in an amount of 1.5 w/v % to 5 w/v %.

4. The nanoemulsion ophthalmic composition of claim 2, wherein the polyoxyethylene castor oil is in an amount of 1.5 w/v % to 5 w/v %.

5. The nanoemulsion ophthalmic composition of claim 1, wherein the nanoemulsion ophthalmic composition has an average particle size of 1 nm to 100 nm.

6. The nanoemulsion ophthalmic composition of claim 1, further comprising at least one stabilizer selected from the group consisting of carboxymethyl cellulose (CMC), hydroxypropyl methylcellulose (HPMC), hydroxyethyl cellulose (HEC), polyvinyl alcohol (PVA), polyvinyl pyrrolidone (PVP), carbomer, gellan gum, xanthan gum, hyaluronic acid (HA), sodium hyaluronate, sodium alginate, and dextran.

7. The nanoemulsion ophthalmic composition of claim 6, wherein the stabilizer is in an amount of 0.001 w/v % to 10.0 w/v %.

8. A method for preparing a stable nanoemulsion ophthalmic composition with low ocular irritation, the method comprising stirring and mixing:
   cyclosporine in an amount of 0.07 w/v % to 0.2 w/v %;
   castor oil in an amount of 0.2 w/v % to less than five times the amount of cyclosporine;
   a hydrophilic emulsifier comprising polyoxyethylene castor oil in an amount of 1 w/v % to 5 w/v %;
   at least one hydrophobic emulsifier selected from the group consisting of polyethylene glycol and propylene glycol in an amount of 0.1 w/v % to 5 w/v %;
   menthol in an amount of 0.001 w/v % to less than 0.1 w/v %; and
   an aqueous solvent,
   whereby a stable nanoemulsion ophthalmic composition with low ocular irritation is prepared.

9. The method of claim 8, wherein the castor oil is in an amount of 0.25 w/v % to less than five times the amount of cyclosporine.

10. The method of claim 8, wherein the polyoxyethylene castor oil is in an amount of 1.5 w/v % to 5 w/v %.

11. The method of claim 9, wherein the polyoxyethylene castor oil is in an amount of 1.5 w/v % to 5 w/v %.

12. The method of claim 8, wherein the nanoemulsion ophthalmic composition has an average particle size of 1 nm to 100 nm.

13. The method of claim 8, further comprising mixing a stabilizer into the nanoemulsion ophthalmic composition.

14. The method of claim 13, wherein the stabilizer is in an amount of 0.001 w/v % to 10.0 w/v %.

15. A stable nanoemulsion ophthalmic composition with low ocular irritation, which is prepared by mixing:
   cyclosporine in an amount of 0.07 w/v % to 0.2 w/v %;
   castor oil in an amount of 0.2 w/v % to less than five times the amount of cyclosporine;
   a hydrophilic emulsifier comprising polyoxyethylene castor oil in an amount of 1 w/v % to 5 w/v %;
   at least one hydrophobic emulsifier selected from the group consisting of polyethylene glycol and propylene glycol in an amount of 0.1 w/v % to 5 w/v %;
   menthol in an amount of 0.001 w/v % to less than 0.1 w/v %; and
   an aqueous solvent.

16. The nanoemulsion ophthalmic composition of claim 15, wherein the castor oil is in an amount of 0.25 w/v % to less than five times the amount of cyclosporine.

17. The nanoemulsion ophthalmic composition of claim 15, wherein the polyoxyethylene castor oil is in an amount of 1.5 w/v % to 5 w/v %.

18. The nanoemulsion ophthalmic composition of claim 16, wherein the polyoxyethylene castor oil is in an amount of 1.5 w/v % to 5 w/v %.

19. The nanoemulsion ophthalmic composition of claim 15, wherein the nanoemulsion ophthalmic composition has an average particle size of 1 nm to 100 nm.

20. The nanoemulsion ophthalmic composition of claim 15, wherein the nanoemulsion ophthalmic composition is prepared by further mixing a stabilizer therein.

21. The nanoemulsion ophthalmic composition of claim 20, wherein the stabilizer is mixed in an amount of 0.001 w/v % to 10.0 w/v %.

22. A method for treating dry eye syndrome, the method comprising administering to a subject a stable nanoemulsion ophthalmic composition with low ocular irritation comprising:
   cyclosporine in an amount of 0.07 w/v % to 0.2 w/v %;
   castor oil in an amount of 0.2 w/v % to less than five times the amount of cyclosporine;
   a hydrophilic emulsifier comprising polyoxyethylene castor oil in an amount of 1 w/v % to 5 w/v %;
   at least one hydrophobic emulsifier selected from the group consisting of polyethylene glycol and propylene glycol in an amount of 0.1 w/v % to 5 w/v %;
   menthol in an amount of 0.001 w/v % to less than 0.1 w/v %; and
   an aqueous solvent.

* * * * *